United States Patent [19]

Remijan

[11] 4,410,244

[45] Oct. 18, 1983

[54] RETINAL ACUITY TESTING DEVICE

[75] Inventor: Paul W. Remijan, Southbridge, Mass.

[73] Assignee: Randwal Instrument Co., Inc., Southbridge, Mass.

[21] Appl. No.: 240,200

[22] Filed: Mar. 3, 1981

Related U.S. Application Data

[62] Division of Ser. No. 863,948, Dec. 23, 1977, Pat. No. 4,265,534.

[51] Int. Cl.³ .............................................. A61B 3/10
[52] U.S. Cl. ................................ 351/211; 350/162.2; 351/222; 356/354
[58] Field of Search ................ 351/6, 13, 14, 17, 205, 351/211, 214, 222; 350/3.7, 162 R, 162.20; 356/353, 354, 356

[56] References Cited

U.S. PATENT DOCUMENTS 3,468,609  9/1969  Sterrett et al. ...................... 356/353
3,787,117  1/1974  Watkins .............................. 356/354
4,009,940  3/1977  Ohzu ..................................... 351/14
4,025,197  5/1977  Thompson .......................... 356/356
4,125,320  11/1978  Rassow et al. ........................ 351/14

Primary Examiner—R. A. Rosenberger
Attorney, Agent, or Firm—Cesari and McKenna

[57] ABSTRACT

Optical measuring and testing apparatus incorporating a holographically recorded, single-frequency, optically thin phase grating. When this phase grating is illuminated by a quasi-monochromatic spatially coherent light source, it acts as a basic common path interferometer and constitutes a highly efficient source for a high contrast, stable, interference fringe pattern. In one embodiment, elements are repositioned to move the light source with respect to the grating thereby to alter the number of fringes in a given area. In another embodiment, elements are rotated about the optical axis of the apparatus to control the orientation of the fringe pattern. Provision is also made for allowing the examiner to view the patient's eye pupil during testing.

10 Claims, 8 Drawing Figures

FIG.1

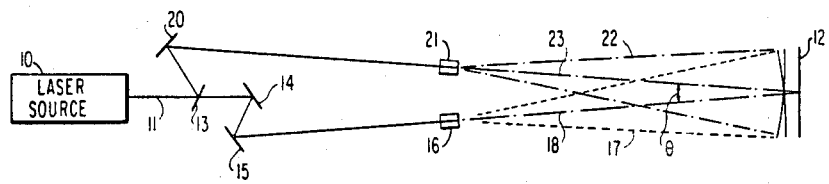

FIG 2

STEP 1
EXPOSE PHOTOGRAPHIC EMULSION TO LASER TWO BEAM INTERFERENCE PATTERN

STEP 2
DEVELOP EMULSION

STEP 3
STOP DEVELOPMENT WITH ACID HARDENER

STEP 4
FIX AND HARDEN EMULSION

STEP 5
HYPO-CLEAR EMULSION

STEP 6
WASH EMULSION IN FILTERED WATER

STEP 7
RINSE EMULSION IN METHANOL TO REMOVE SENSITIZING DYE – THEN DRY

STEP 8
BLEACH EMULSION IN $Br_2$ VAPOR

STEP 9
RINSE EMULSION IN METHANOL TO REMOVE RESIDUAL $Br_2$ – THEN DRY

FIG 5

A 

B 

C 

D 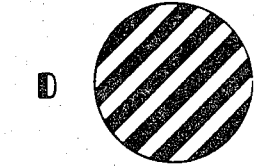

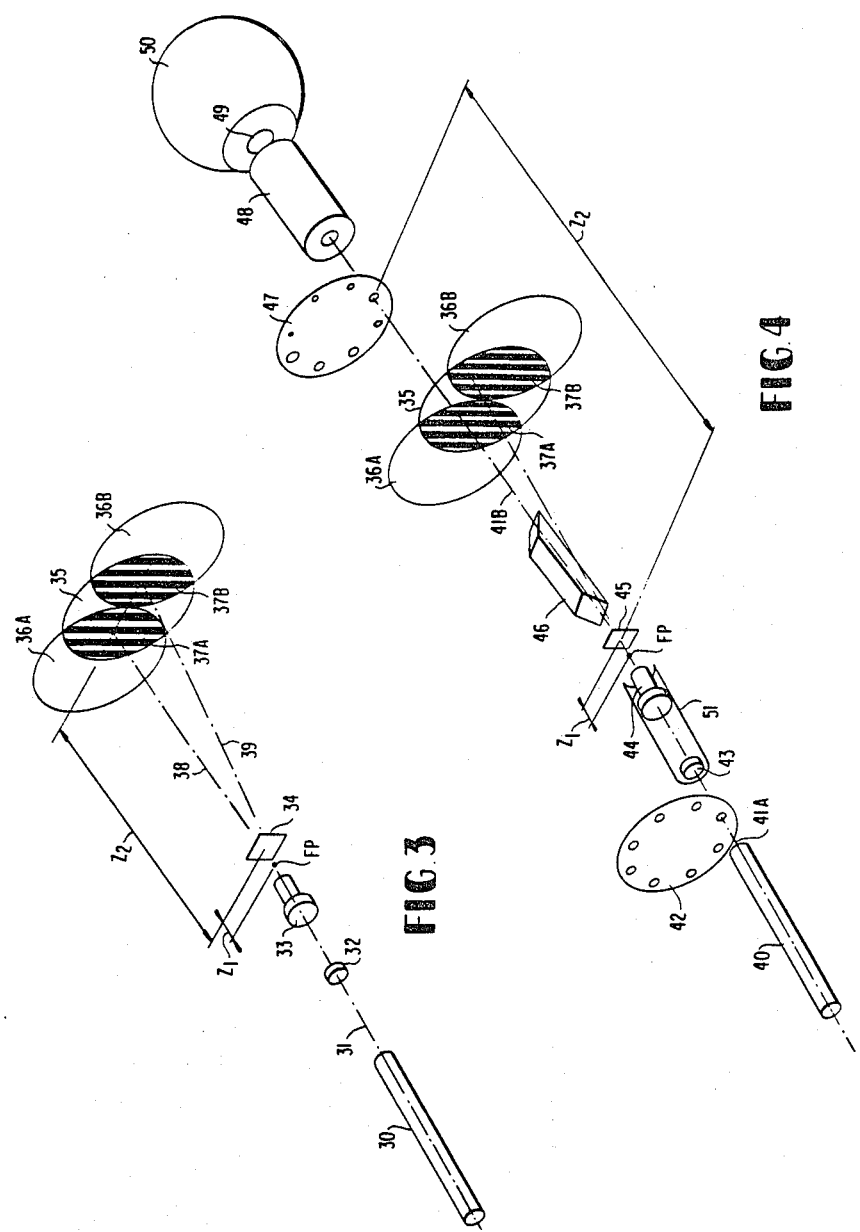

RETINAL ACUITY TESTING DEVICE

CROSS REFERENCE TO RELATION APPLICATION

This is a division of by co-pending U.S. patent application Ser. No. 863,948, filed Dec. 23, 1977 and assigned to the same assignee as the present invention, now U.S. Pat. No. 4,265,534.

BACKGROUND OF THE INVENTION

This invention generally relates to the field of optical measuring and testing, and more specifically to apparatus incorporating interference fringe pattern generators for retinal acuity testing.

There are two basic methods for producing fringe patterns: (1) an interferometric technique that utilizes interference phenomena, and (2) a Moire technique that utilizes shadow casting and/or pattern multiplication.

There are a wide variety of measuring and testing procedures that utilize interference fringe patterns and there are many ways to produce and control inteference fringes. Generally, an interference fringe pattern is produced when at least two coherent beams of light are brought together and interact. When two coherent beams interact, they destructively interfere to produce dark spots or bands and constructively interfere to produce bright spots or bands.

Moire fringes are produced when two similar, geometrically regular patterns consisting of well defined clear and opaque areas are juxtaposed and transilluminated. Some examples of geometrically regular patterns used to generate Moire fringes include (1) Ronchi rulings, (2) sets of concentric circles, and (3) radial grids. The generation of Moire fringes can be considered as shadow casting; that is, the shadow of the first pattern falling onto the second pattern produces the Moire fringes. The mathematical function describing Moire fringes is obtained by multiplying the intensity transmissions or irradiances of the overlapped geometrically regular patterns.

Fringes generated by both interference and Moire techniques are used by ophthalmologists for testing retinal acuity. In one such apparatus, light from a laser is divided into two coherent beams by an optical element consisting of two adjoined dove prisms. These two beams are converged and directed into the eye where they interact to produce an interference fringe pattern on the retina.

In another apparatus used in the field of ophthalmology a laser source and an ordinary Ronchi ruling form an interference fringe pattern. The laser source produces a laser beam that is directed to the Ronchi ruling. The Ronchi ruling splits the incident beam into multiple coherent beams of widely varying strengths. It is necessary to use complicated motions of numerous optical and mechanical components to select only two coherent beams and to control the spacing of interference fringes eventually projected onto the retina. In yet another ophthalmic apparatus, two Ronchi rulings are used. They produce Moire fringes that are eventually imaged onto the retina.

Ophthalmologists use apparatus that implements either the Moire or interference techniques to test and measure retinal acuity. This measurement is obtained by varying the "fineness" of the fringes projected onto the retina and monitoring the patient's ability to resolve them. The patient's ability to resolve a fringe pattern of a certain "fineness" converts directly into a measurement of retinal acuity.

Certain disadvantages exist in apparatus that utilize the interferometric techniques to form fringe patterns in ophthalmic applications. For example, in such apparatus, the two light beams generally travel through different light paths that contain distinct optical elements. If the elements in each path are not matched optically, aberrations distort the fringe pattern. Matched optical elements can eliminate the aberration problem; however, they significantly increase the overall expense of the apparatus. Moreover, this apparatus is subject to various outside influences, such as vibration and thermal change. These influences can cause fringe pattern motion or noise and lead to improper measurements.

Moire techniques also have many limitations. When small spacings and high accuracies are required, the geometrically regular patterns used to generate Moire fringes are quite difficult and expensive to produce. In applications where one ruling moves next to a fixed ruling, the spacing between the rulings must be held constant or errors result. Also, Moire fringes are localized, i.e., they exist in a very small region of space, and additional optical components are often required to image the Moire fringes into desired regions.

Recently, an amplitude grating and a spatially coherent, quasi-monochromatic light source have been used to generate interference fringes. An amplitude grating is a generally transparent to semi-transparent media whose opacity is altered in accordance with some spatially periodic pattern. An amplitude grating "breaks up" or diffracts an incoming beam of light into a series of diffracted cones or orders. The strength, or amount, of light in each order depends upon the exact shape of the periodic opacity of the amplitude grating. Although various diffracted orders could be approximately the same strength, scalar diffraction theory for a thin amplitude grating predicts that the dominant strength will lie in the zero order undiffracted light and that the strength of other diffracted orders will vary. Indeed, practical applications bear out this prediction.

In U.S. Pat. No. 3,738,753, issued June 12, 1973, Huntley proposes to pass light from a source through an amplitude grating to produce different order cones of diffracted light: for example, zero order and first order cones. To compensate for the different intensities, the diffracted light cones are reflected back through the grating. After the second passage through the grating, the zero order cone of the reflected first order cone and the first order cone of the reflected zero order cone have equal strengths and are combined to form a high contrast interference fringe field. This double pass system is quite stable because it closely approximates a common path interferometer. In a common path interferometer the interfering beams traverse the same optical path. Therefore, perturbations affect both beams simultaneously and do not distort the output fringe pattern which is sensitive only to differences between the two optical paths. However, problems in such a double pass system do occur because it is difficult to control grating substrate aberrations and mirror-grating separation.

Further improvements have been made with the advent of holographically produced amplitude gratings. Holographic amplitude gratings are produced by exposing a high resolution photographic emulsion to the precise interference pattern of a laser two-beam interferometer. During ordinary photographic processing, the photosensitive silver halide in the emulsion converts into opaque metallic silver to form the amplitude grating.

In an application of one such holographic grating, a double frequency holographic grating produces a so called "shearing" pattern. See U.S. Pat. No. 3,829,219, issued 1974 to Wyant, and No. 4,118,124 issued Oct. 3, 1978 to Matsuda. This grating is produced by sequentially exposing a single photographic emulsion to a first laser interference pattern of a first spatial frequency, $f_1$, and then to a second laser interference pattern of a second spatial frequency, $f_2$. Equal amplitude transmission modulations at both frequencies $f_1$ and $f_2$ are achieved by adjusting the exposure to the first and second laser patterns. Ordinarily, the two sequential exposures are identical, but if $f_1$ and $f_2$ are very different or if one laser pattern is in red light and the other is in green light, the sequential exposures must be compensated for the spectral and frequency responses of the photographic plate. These exposure adjustments to achieve equal amplitude transmission modulations in $f_1$ and $f_2$ are usually done by trial and error.

Upon illumination with spatially coherent, quasimonochromatic light, this double frequency grating produces two first order light cones of equal strength, one light cone being associated with each of the $f_1$ and $f_2$ frequencies. These two first order light cones interact to form a very stable, high contrast fringe pattern. Such a double frequency holographic shearing interferometer also is a common path interferometer. It is simple to construct. However, in this interferometer it is necessary to separate the zero order cone from the interacting first order cones. The separation requirement limits the f/number of the input light cone and the amount of shear obtainable. Moreover, if the two first order cones have high diffraction angles an astigmatic distortion of the output fringe field exists. In addition, the efficiency, or ratio of output fringe field power to input power, is only about 2%.

For many years people have bleached photographically recorded amplitude gratings to obtain "phase gratings". One basic type of such bleaching, known as volume bleaching, chemically converts the opaque silver in the photographic emulsion into a transparent, high index silver salt. A second type of bleaching, known as tanning, chemically removes the developed silver within the emulsion and leaves a void. A tanned phase grating has a corrugated surface. Whereas an amplitude grating selectively absorbs light, a bleached phase grating selectively introduces phase delays across the input light beam. As a result, a phase grating is much more efficient than an amplitude grating; that is, the ratio of first order power to input power is greater.

However, bleached gratings are generally characterized by substantial problems. They are very noisy and also may deteriorate physically back into amplitude gratings upon extended exposure to light. Bleached gratings also have a lower spatial frequency response than amplitude gratings. Although volume bleached gratings are less noisy and have a higher spatial frequency response than their tanned counterparts, they generally are weaker and less efficient.

The efficiency of a volume bleached grating can be increased by increasing its thickness. However, any substantial increase in thickness drastically changes the basic diffraction properties of the grating. Any amplitude or phase grating can be considered optically thick when the optical thickness of the emulsion is more than five times the grating spacing. A grating can be considered optically thin if the optical thickness of the emulsion is less than half the grating spacing. Properties of thick gratings are accurately predicted by electromagnetic theory, while properties of thin gratings are described by scalar diffraction theory. For example, a thick phase grating output consists of only the zero order and one first order diffracted cone. In addition, diffraction takes place only for a plane wave input at a certain specified angle with respect to the grating. On the other hand, a thin grating of the same spacing produces multiple orders (i.e. the 0, $\pm 1$, $\pm 2$, $\pm 3$, etc. orders) with either a spherical wave or plane wave input at an arbitrary angle with respect to the grating.

Distinctions between optically thin amplitude and optically thin phase gratings are accurately predicted by scalar diffraction theory. When a pure sinusoidal amplitude transmission perturbation exists in a thin amplitude grating, only the zero and $\pm 1$ diffracted orders exist. When a pure sinusoidal phase perturbation occurs in a thin phase grating, many orders (e.g., the 0, $\pm 1$, $\pm 2$, $\pm 3$, and other orders) are observed. The strengths of the phase grating orders are proportional to the normalized Bessel functions $[J_n (m/2)]^2$, where n is the order number (e.g., n equals 0, $\pm 1$, $\pm 2$, ...) and m is the strength of size of the phase perturbation in radians. When the amplitude grating perturbation departs from a pure sinuosoidal form, additional diffracted orders are generated. The strengths of these additional orders are directly related to the strengths of the Fourier components associated with the grating perturbation function.

With a phase grating, the diffracted orders associated with a non-sinusoidal phase perturbation are predicted by convolving the individual outputs from each Fourier component of the phase perturbation. Such a multiple convolution reveals complicated phase relationships between multiple orders associated with just one particular Fourier component. In addition, diffracted orders corresponding to sum and difference frequencies are generated when the phase perturbation consists of more than one fundamental spatial frequency. For example, one might consider bleaching the previously discussed double-frequency holographic grating to improve its poor efficiency. Although bleaching will increase the overall efficiency of such a grating, the bleached grating, in accordance with the convolutional operation, produces sum and difference frequency diffraction cones that are in addition to and that interact with the desired fundamental frequency diffraction cones. It is then possible for the sum and difference frequency diffraction cones to destroy the fringe field.

SUMMARY

Therefore, it is the object of this invention to provide an improved holographic phase grating for producing a high contrast interference pattern that is useful in opthalmic applications.

Another object of this invention is to provide an improved holographic grating that is useful in a number of applications including the testing of retinal acuity.

Yet another object of this invention is to provide apparatus for testing retinal acuity.

In accordance with my invention, I use a single frequency holographic phase grating in a retinal acuity tester. A quasi-monochormatic light source illuminates the grating to produce diverging diffractions, in conical form, of different order. In two diffractions of different order, the diffractions have equal strength and overlap thereby to produce a bright, high contrast, low noise interference pattern. I place a focusing element between the light source and grating for producing a point source of light at a focal point that is slightly displaced from the grating. Other optical elements positioned in the resulting interference fringe field project the interference pattern through the eye and onto the retina. The fineness of the pattern on the retina is controlled accurately by positioning the focal point with respect to the grating. This system can accurately measure retinal acuity in the presence of corneal or eye lens opacities known as cataracts.

This invention is pointed out with particularity in the appended claims. The above and further objects and advantages of this invention may be better understood by referring to the following description taken in conjunction with the accompanying drawings.

BRIEF DESCRIPTION OF THE DRAWINGS

FIG. 1 is a diagram that illustrates the apparatus for producing a holographic grating in accordance with this invention;

FIG. 2 is a chart that depicts the various basic steps for processing a holographic grating in accordance with this invention;

FIG. 3 is a diagram of an interferometer constructed in accordance with one aspect of this invention for producing fringe patterns;

FIG. 4 is a diagram of apparatus constructed in accordance with this invention for measuring retinal acuity;

FIG. 5 depicts typical fringe patterns that are produced in the retinal acuity apparatus shown in FIG. 4;

DESCRIPTION OF ILLUSTRATIVE EMBODIMENTS

A. Holographic Grating

Figure 6:
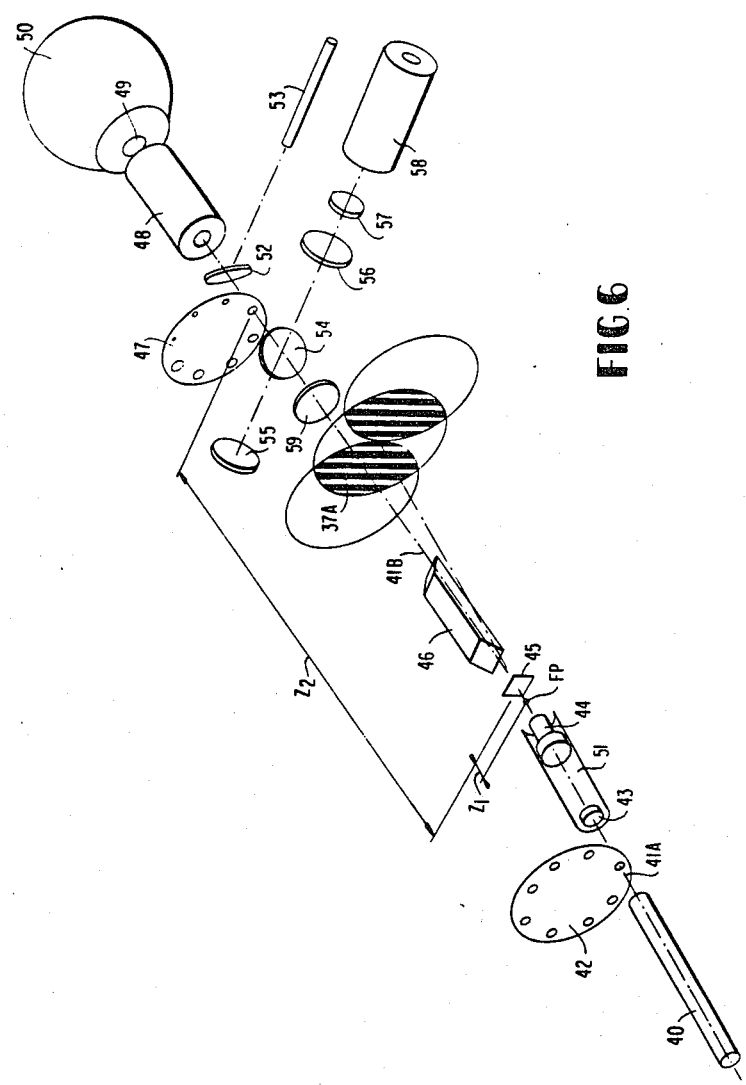
FIG. 6 is a diagram for an alternate embodiment of retinal acuity testing apparatus constructed in accordance with this invention.

FIG. 1 depicts, in diagrammatic form, the arrangement of apparatus necessary for exposing a photographic plate during the production of a holographic phase grating. The holographic phase grating produced in accordance with the arrangement shown in FIG. 1 and the procedures outlined in FIG. 2 are essential to the operation of the diverse embodiments of the invention that are shown in the other Figures. Specifically, this apparatus includes a laser source 10 which directs light along an axis 11. The other apparatus in FIG. 1 splits the light into parts that travel over two separate paths and are then brought back together to expose a photographic plate 12.

A conventional beamsplitter 13 separates the light into two parts. A first part travels along a first path that includes mirrors 14 and 15 for reflecting the light into an objective lens and pinhole 16, thereby to produce a spherical wave that emanates from a point source at the pinhole. The wave appears in a cone 17 and is directed toward the photographic plate along an axis 18. The second path established by the beamsplitter 13 includes a mirror 20 and an objective lens and pinhole 21 that produce a spherical wave cone 22 that emanates from a point source at that pinhole along an axis 23. The light waves from these two point source combine; they destructively interfere to produce dark bands and constructively interfere to produce bright bands at the photographic plate 12.

The photographic plate 12 mounts on a rotary table which positions the photographic plate 12 and accurately establishes an angle $\theta$ between the axes 18 and 23. The spatial frequency, $\xi$, of the interference pattern at plate 12 is closely approximated by the equation $$\xi = \frac{2 \sin (\theta/2)}{\lambda}, \qquad (1)$$

where $\lambda$ is the laser wavelength. Although the fringes produced at the plate 12 are slightly hyperbolic, they are excellent approximations to rectilinear bands and therefore are shown as such in various Figures. Increasingly better approximations to rectilinear bands are achieved by increasing the distance along the axes 18 and 23 between the plate 12 and the pinholes 16 and 21, respectively.

The apparatus diagrammed in FIG. 1 has been used to manufacture gratings having the desirable properties that characterize my invention. The equipment is simple and relatively inexpensive. For example, the laser 10 can comprise a $TEM_{00}$ mode laser; the beamsplitter 13, a conventional variable density beamsplitter that enables the intensity of the two beams to be equalized. The mirrors 14, 15 and 20 are standard planar mirrors. The objective lens comprises a conventional $10\times$ microscope objective, and the pinhole matches that objective lens. The distances 18 and 23 are approximately 2 meters. With this specific arrangement, I am able to obtain a 500 line-per-millimeter interference fringe pattern over a $3'' \times 3''$ area with maximum fringe displacement error of about 0.00254 millimeters.

Once the apparatus in FIG. 1 is arranged, the emulsion on the photographic film can be exposed to the interference pattern as shown as Step 1 in FIG. 2. During this exposure step, certain controls must be exercised to assure a holographic grating of good quality. For example, the exposure should be made in an environment that is not subjected to vibrations. Thermal disturbances should be minimized as any air flow between the beamsplitter 13 and the photographic plate 12 can distort the resulting fringes. In applications where very high densities and minimal distortions are required the distances along axes 18 and 23 must be increased to 5 or even 10 meters. Precise determinations of $\lambda$ and $\theta$ must be made. Although this basic apparatus can be used to produce highly accurate holographic phase gratings, the maximum accuracy ultimately then will be determined by the accuracy of angular measuring equipment, the stability of the single frequency laser, the optical table stability, and the atmospheric and thermal controls that are exercised.

In order to produce a phase grating with special properties that enable the construction of the various disclosed embodiments, it is first necessary to produce an amplitude grating. Given the various properties of commercially available photographic emulsions and developers, a thin emulsion photographic plate and a chemically compatible developer are selected. A process of heavily overexposing and underdeveloping the emulsion reduces the optical thickness of the processed emulsion to a fraction of its original physical thickness. Thus, by utilizing the controls set forth in steps 1 and 2 of FIG. 2, one produces an amplitude grating characterized by having:

1. an optically thin emulsion conforming to scalar diffraction theory;
2. a specific form for the absorbtion function which converts to a correspondingly specific phase transmission function after bleaching; and
3. a specific amplitude or strength of the absorbtion function which converts to a specific peak to peak phase modulation after bleaching.

Specific plate types, exposures, development times and developers are discussed later.

Once the development of step 2 is complete, the photographic plate is washed in an acid short-stop solution is step 3. The solution contains an acid hardener. A two-minute treatment in a hardening bath produces acceptable results.

In step 4, the emulsion of the photographic plate is fixed and hardened. A standard fixing bath and acid hardener have been used successfully, the plate being immersed in the bath for about ten minutes.

Next (step 5) the emulsion is prewashed for thirty seconds and hypo-cleared in a hypo clearing bath for about two minutes. In step 6, the emulsion is washed (e.g., twenty minutes in filtered water) and then soaked in a methanol bath until all residual sensitizing dye is removed (step 7). Once the methanol bath has been completed, the plate is dried in a light blow air drying operation.

All the foregoing steps are conventional photographic processing steps that utilize commericially available chemicals. Upon completion of step 7, an amplitude grating has been produced. Steps 8 and 9 then convert this amplitude grating into a phase grating having the desired characteristics.

More specifically, after the photographic plate is dried thoroughly in step 7, it is bleached during step 8 in a bromine vapor until the plate is clear. Once the bleaching operation has been completed, the plate is rinsed in a methanol bath to remove residual $Br_2$ and dried thoroughly by a light blow air drying operation in step 9.

It now will be beneficial to discuss certain characteristics of these holographic phase gratings that are particularly desireable. First, the exposure and development times and the emulsion have been chosen to produce "thin" gratings. As a specific example, I have made 393.7 line-per-millimeter gratings on Kodak 131-01 plates according to the foregoing processing procedure using an average exposure of 200 ergs/cm$^2$ and a development time of 15 seconds in standard Kodak D-19 developer at 80° F. Uniform development is achieved by using a large development tank and rapid manual agitation of the plate. After complete processing in accordance with the steps of FIG. 2, the resulting thin phase grating diffracts both input spherical waves as well as input plane waves; as previously stated, a thick grating diffracts only input plane waves incident at a particular angle with respect to the grating.

Measurements have shown that a thin phase grating manufactured according to the foregoing process has a pure sinusoidal phase transmission function whose peak-to-peak phase delay produces equal strength zero and ±1 diffraction orders. The 200 ergs/cm$^2$ exposure produces an average amplitude transmission of approximately 0.45 for the developed, but unbleached, Kodak 131-01 plates. Experimental data has confirmed that a pure sinusoidal phase transmission function is maintained when the thin grating has an average amplitude transmission of 0.5 or less in its developed but unbleached state. The strength or peak-to-peak phase delay of the final phase grating is adjusted by controlling the initial exposure (Step 1, FIG. 2) within the limits set by an average amplitude transmission of 0.5 (measured after Step 7 in FIG. 2). A very weak phase grating produced with low exposure levels exhibits a strong zero order diffraction, a weak first order, and an even weaker second order. Stronger gratings produced with higher exposure levels exhibit increasingly more powerful first and second order diffraction and decreased zero order diffraction. Equal strength zero and ±1 diffraction orders or equal strength zero and ±2 diffraction orders are achieved by a trial and error adjustment of the initial exposure.

The advantages of such a thin phase grating that produces two different diffraction orders of equal strength will now become apparent in the following discussion of an interferometer that utilizes such a phase grating.

B. Interferometer

Referring now to FIG. 3, an interferometer is depicted in schematic form that includes a helium neon laser 30 which directs light along an axis 31 to a negative lens 32. The negative lens 32 expands the beam slightly so that it completely fills a microscope objective 33. The microscope objective 33 focuses this light at a focal point FP displaced a distance $Z_1$ from a holographic grating 34 constructed as described above. The laser 30, negative lens 32 and microscope objective 33 constitute a source of a quasi-monochromatic diverging spherical wave that emanates from the focal point FP. In one embodiment, the cone from the focal point FP is an f/2 cone.

When the spherical wave from the point source at the focal point FP strikes the grating 34, it produces a number of cones of diffraction. According to scalar diffraction theory, the strength of the diffracted cones is governed by the Bessel function $[J_n(m/2)]^2$, where n is the diffraction order number and m is the grating transmission function peak-to-peak phase delay in radians. The previously specified exposure and development times yield a value of m=2.870 at =6328 Å. The zero and first order diffraction cones are of equal intensity because $[J_0(1.435)]^2 = [J_1(1.435)]^2$. Moreover, the diffraction angles are such that the zero order cone overlaps both first order cones, while the first order cones merely abut each other. At some point at a distance $Z_2$ from the grating 34, an output such as is shown in FIG. 3 is produced. The zero order cone appears as planar circle 35; first order cones appear as planar circles 36A and 36B. Areas 37A and 37B are areas of overlap and the fringes are produced in those areas. Moreover, the fringes in the areas 37A and 37B are out of phase with each other. Thus, if the centrally located fringe in area 37A is a dark band, the corresponding fringe in area 37B is a light, or bright, band. By "light" and "dark" bands, I do not means bands having the same intensity across the band, as the bands are shown in the drawings. The fringe intensity actually varies smoothly and is proportional to the square of a sine function, although the eye may perceive distinct alternating bands under some illumination conditions.

The 180° phase shift between the fringes in areas 37A and 37B is a direct result of having a pure sinusoidal phase transmission function associated with grating 34. When the phase transmission function of 34 departs from a pure sinusoid, the fringes in the areas 37A and 37B will have some other phase relationship not equal to 180°. The 180° phase shift is not essential to the production of high contrast fringe patterns; but it is important in a position detecting application where quadrature electrical signals are derived from the central fringes. Control of the grating transmission function form is achieved by selecting the proper combination of emulsion, developer, exposure and development time as previously discussed.

The interferometer shown in FIG. 3 has several properties. If the distance $Z_1$ is varied, the number of fringes within the overlap areas 37A and 37B changes. Specifically, decreasing the distance $Z_1$ decreases the number of fringes that appear in the overlap areas. As $Z_1$ is varied, fringes "flow" into or out of the areas 37A and 37B. Although this "fringe flow" may cause the central fringes to widen or narrow, it does not move the central fringes; they remain located at the centers of their respective areas. The importance of this central fringe behavior with $Z_1$ variations will be discussed later. If the grating 34 is moved in a plane that is normal to the axis 31 and perpendicular to the direction of the fringes, all the fringes in the areas 37A and 37B appear to slide through those areas, but the number of fringes in those areas remains unchanged. If the distance $Z_2$ varies, the number of fringes also remain the same, but in this case their sizes change, the fringe widths becoming smaller as $Z_2$ decreases. The interferometer parameters are related by the equation:

$$T=(Z_2+Z_1)/\xi Z_1 \qquad (2)$$

Where T is the fringe period in overlap regions 37A and 37B, $\xi$ is the spatial frequency of the grating 34 defined by equation (1) and $Z_1$ and $Z_2$ are the positive distances shown in FIG. 3.

The holographic grating interferometer in FIG. 3 is very stable and free of fringe distortion from outside influences because it is essentially a common path interferometer. Atmospheric changes, air currents and thermal instabilities do not distort the fringes. Moreover, the intensity of the light in each of the diffraction cones is much greater than that usually obtained from amplitude gratings because the phase grating essentially is transparent and relies entirely on time delays within the grating 34 to produce the diffraction cones. As a result the overall brightness of the fringe pattern is increased. Moreover, as the intensities in each of the zero-order and first-order cones are equal, the destructive and constructive interferences tend to be complete so the dark bands are essentially black while the bright bands are essentially twice as bright as the average light. Thus the grating enables the production of a simple common path interferometer that produces bright, high-contrast fringes.

The foregoing properties lay a basis for understanding the application of a bleached phase grating in a retinal acuity tester. In this tester, the distance $Z_1$ is intentionally varied to alter the number of fringes that appear in a given area and impinge the retina. Apparatus that is particularly adapted for use in a retinal acuity tester is discussed with reference to FIGS. 4 through 7B.

C. Retinal Acuity Tester

The retinal acuity tester in FIG. 4 includes a laser 40 that can comprise a low-power TEM$_{00}$ mode helium neon cylindrical or other like laser. Light from the laser is directed along an axis 41A through a filter wheel 42. The filter wheel 42 contains a number of conventional metallic coated neutral density filters. These filters control the intensity of the light that is transmitted to the remaining elements in the retinal acuity tester. In this manner it is possible to control the brightness of the fringes eventually projected onto a patient's retina.

A negative lens 43 and microscope objective lens 44 that are movable along the axis 41A focus the light at a focal point FP. The negative lens 43 expands the beam from the laser slightly so as to completely fill the microscope objective lens 44 aperture with a uniform light distribution. A −4 mm focal length biconcave lens is a satisfactory negative lens. The microscope objective 44 is a conventional objective lens, a 10× N.A. 0.25 objective lens being satisfactory.

The grating 45 comprises a holographically recorded, single frequency phase grating that is produced as described earlier. The grating frequency is 400 1/mm (lines per millimeter) to allow for ideal separation of zero and ±1 orders from the N.A. 0.25 objective input cone. The grating 45 also is optically thin, and the zero and first order diffractions have equal strengths. As becomes apparent later, there is no reason to control the phase of output fringes from the grating 45 when the grating is used in a retinal acuity testing apparatus. Therefore, the added constraints in the processing procedure associated with preserving a pure sinusoidal phase perturbation are eliminated. A convenient development time compatible with the requirement of producing an optically thin emulsion is chosen. Then exposure time is adjusted by trial and error until the desired strength of phase modulation is achieved. In this case, a modulation producing equal strength zero and ±1 orders is obtained. Thin, very clean, low noise, 400 1/mm phase gratings for the retinal acuity tester can be produced on Kodak 120-01 plates using an average exposure of 1000 ergs/cm$^2$ at 6328 A. These plates are developed for 100 seconds in Kodak D-19 developer at 68° F. (steps 1 and 2 in FIG. 2). Steps 3 through 9 in FIG. 2 are used to complete the processing.

The grating 45 produces the diverging cones of different order diffractions. More specifically, there is a zero order cone represented by circle 35 and first order cones represented by abutting circles 36A and 36B. These cones are of equal strength so that they produce high contrast fringes as shown in areas 37A and 37B where the zero and first order cones overlap. In this specific embodiment, an axis 41B extends from the center of the grating 45 through the center of the area 37A. A dove prism 46 is positioned to receive the fringe field and is disposed with its longitudinal axis on the axis 41B. As the dove prism 46 is rotated about its longitudinal axis, the angle of fringe orientation within the fringe field 37A also rotates about the axis 41B through twice the prism rotation angle.

The fringe field propagates through the dove prism 46 to an aperture wheel 47. One aperture in the aperture wheel 47 is selectively aligned with the axis 41B by rotating the aperture wheel 47. An eyepiece 48 receives light transmitted through the selected aperture. This eyepiece 48 forms twin point sources within an eye pupil 49 of the patient. These point sources correspond to the point sources formed in FIG. 1 by the objective lenses and pinholes 16 and 21. The fringe field in the area 37A thereupon propagates through the eye and is projected onto the retina 50.

During testing, a patient positions his eye pupil 49 on the axis 41B near the eyepiece 48 to intercept the twin point sources from the eyepiece 48. When his eye is in the proper position, the patient will sense or "see" the fringe pattern projected onto his retina 50. The cornea and eye lens have negligible optical power in such an arrangement and therefore have a negligible effect upon the fringe pattern projected onto the retina.

The negative lens 43 and microscope objective 44 are positioned on a slider 51 that can be moved along the axis 41A thereby to reposition the focal point (FP) with respect to the grating 45. As the slider 51 and focal point (FP) are repositioned, the number of fringes within fringe field 37A changes. The ability of the patient to see or discern a pattern of a given number of fringes within the field projected onto his retina is directly equated to standard measurements of acuity.

During retinal examination, the dove prism 46 and aperture wheel 47 play subtle, but important, roles because the retinal test is rather subjective. The examiner is able to control the orientation of the fringes by rotating the dove prism 46 thereby to determine whether a patient's claim of being able to see a pattern in a certain orientation is actually valid. To the extent that retinal response might exhibit orientational variations, the nature of such variations also can be evaluated.

The diameter of the aperture selected by positioning the aperture wheel 47 controls the size of the retinal area stimulated by the fringe pattern. This field control is important in determining the extent of any macular degeneration. The retinal fields offered by the various apertures in wheel 47 range, in one specific example, from 20° to 0.5°, these fields correspond to circular regions that are stimulated on the retina ranging from 5.0 to 0.155 mm. in diameter.

FIG. 5 illustrates a number of different patterns as they will be perceived by a patient who is being examined utilizing the apparatus shown in FIG. 4. If the slider 51 is located in an intermediate position, the patient could perceive the fringe pattern of alternate dark and bright bands that are shown as pattern A. If a laser that emits red light is used, the light areas are red and the dark areas are black. Thus, the patient perceives a series of straight red and black lines. If the slider 51 is moved along the axis 41A in FIG. 4 toward the grating 45, the number of fringes decreases and the patient perceives pattern B that contains fewer and wider franges. Likewise, motion of the slider 51 in a direction away from the grating 45 beyond the intermediate position increases the number of fringes as shown in pattern C. If, on the other hand, the slider 51 is in the same position that produces pattern A, a 22.5° rotation of the dove prism 46 in FIG. 4 rotates the fringes 45° to an orientation shown in pattern D.

Another embodiment of the retinal acuity tester is shown in FIG. 6. This tester differs from the retinal acuity tester shown in FIG. 4 by the addition of a viewing system for the examiner. This viewing system can be added because the common path principle applies to the overlapped orders producing the area 37A. Various viewing system designs could be used because the choice of specific components is not dictated by fringe distortion considerations. However, the components of the viewing system should be of reasonable quality to insure best viewing system performance.

The viewing system is shown in FIG. 6 includes a beamsplitter 52 that is disposed between the aperture wheel 47 and the eyepiece 48. The beamsplitter 52 directs white light from a fiber optics light guide 53 through the eyepiece 48 onto the eye. The source of light for the light guide can comprise a standard low power fiber optics illuminator (not shown). Light reflected from the eye passes through the eyepiece 48, the beamsplitter 52 and the aperture in aperture wheel 47 aligned with the axis 41B to another beamsplitter 54. Normally, the largest aperture is aligned to provide the largest field of view. The beamsplitter 54 directs this light to a concave mirror 55 that forms a real image of the eye surface near the beamsplitter 54. Lens 56 relays the real image of the eye surface through a polarizer 57 to the focal plane of an eyepiece 58 for observation. The polarizer 57 coacts with another crossed polarizer 59 between the dove prism 46 and the beamsplitter 54 to eliminate that portion of the fringe field reflected from beamsplitter 54 toward eyepiece 58. Viewing system aberrations are reduced by locating the aperture wheel 47 at the center of curvature of mirror 55 and using a symmetrical relay lens 56 at 1:1 conjugates.

Even with good chin rests one of the most frequently encountered problems in ophthalmic examinations is the proper positioning of the patient's eye. With a properly aligned viewing system of the type disclosed in FIG. 6, the exact center of the image observed through eyepiece 58 is centered between the twin coherent point sources formed by eyepiece 48. Thus, when the examiner properly positions a patient's eye pupil to intercept the twin coherent point sources he will observe a clear, centralized image of the eye pupil through eyepiece 58. The viewing system is especially valuable for testing cataract patients because it enables precise location of the twin coherent point sources at any existing opening in a cataract.

Figure 7A:
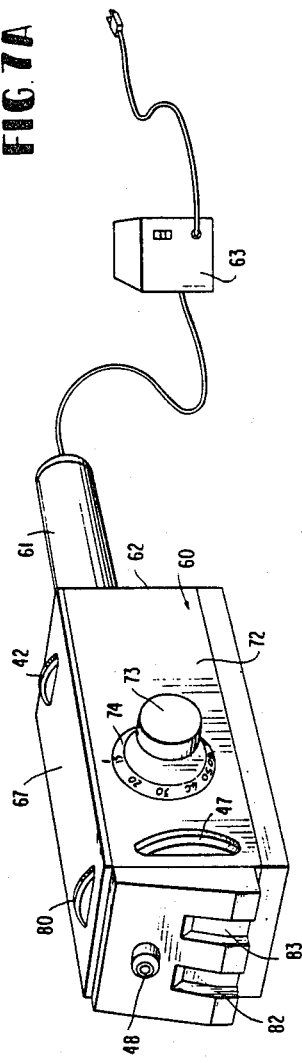
FIG. 7A is a perspective view of a retinal acuity testing apparatus constructed in accordance with this invention.
Figure 7B:
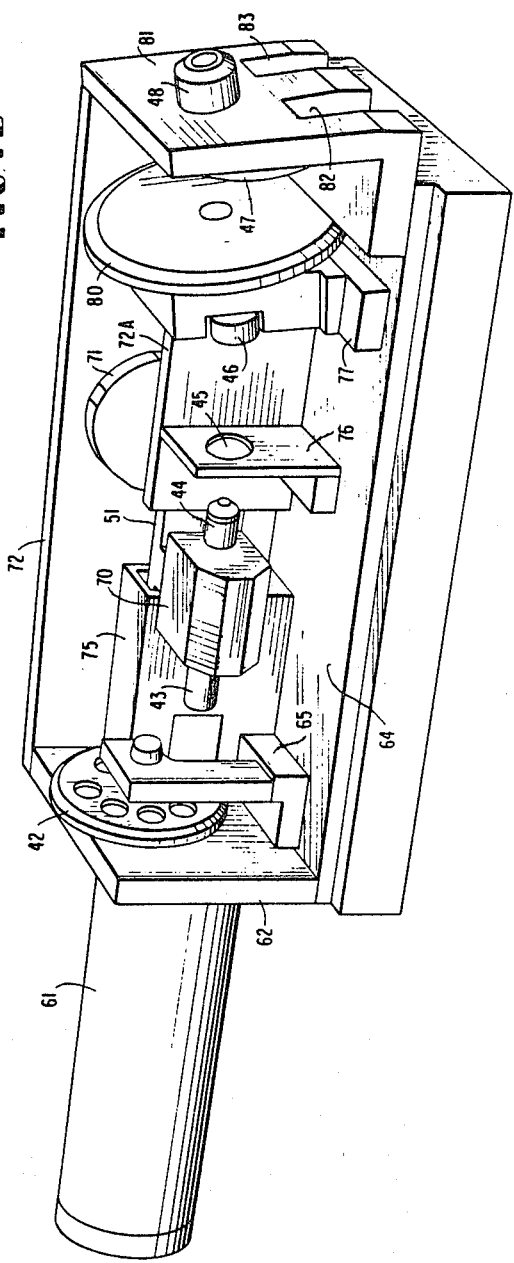
FIG. 7B is a detailed perspective view of the apparatus shown in FIG. 7A with the housing partially removed.

FIGS. 7A and 7B are two views of a retinal acuity tester constructed in accordance with this invention. This specific tester embodies the elements that are disclosed in FIG. 4. More specifically, the tester includes a housing 60 having a conventional laser unit 61 extending from one end 62 of the housing 60. The laser 61 is connected to a conventional laser power supply 63.

The various elements within the housing 60 are supported on a base plate 64. A first element includes an upright stand 65 that supports the filter wheel 42. The examiner rotates a portion of the circumference of the filter wheel 42 that extends through a slot in a top plate 67 of the housing 60 to position the appropriate filter on the light axis. Although the angular position of the filter wheel 42 might be maintained by friction, a more positive positioning means would incorporate some detent indexing mechanism for interacting between the upright stand 65 and the filter wheel 42.

The negative lens 43 and microscope objective lens 44 shown in FIG. 4 are mounted in a housing 70 carried on the slider 51. A rotary cam 71 has a shaft that extends through a side wall 72 of the housing 60 and is supported on a stand 72A. This shaft carries a positioning knob 73, a scale 74 and a detent mechanism that is not shown. The scale 74 is graduated directly in equivalent Snellen acuities ranging from 20/15 through 20/400. As the examiner rotates the knob 73, the cam 71 rotates and longitudinally displaces the slider 51 and both the negative lens 43 and the microscope objective lens 44 thereby to vary the position of the focal point FP shown in FIG. 4. In this embodiment the slider 51 is constituted by a cam follower that contacts the cam 72 and is supported in a slide 75. The slide 75 also houses springs to bias the slider 51 against the cam 71.

Another upright stand 76 is mounted to the base plate 64. This stand 76 carries the grating 45. Thus, when the power supply 63 is activated, the light emanating from the laser 61 passes through the filter wheel 42, the negative lens 43, the microscope objective lens 44 to the grating 45 thereby to produce zero and first order diffraction cones that have equal strengths and that overlap. In one specific arrangement the distance between the grating 45 and the focal point varies over a range from about 0.6 mm to 25 mm. That range of distances enables the apparatus to produce fringe patterns that correspond to acuity measurements from 20/400 through 20/15.

There is also located at a fixed position on the base plate 64 another stand 77. This stand is skewed slightly with respect to the housing 60 in order to position the longitudinal axis of the dove prism 46 on the axis 41 B shown in FIG. 4. The stand 77 carries a rotatable wheel 80. A portion of the wheel 80 extends through another slot in the top 67. The wheel 80 carries the dove prism 46 so that rotation of the wheel 80 by the examiner rotates the dove prism 46 and changes the orientation of the fringes, as shown in pattern D of FIG. 5.

The next element in the tester is an end wall 81 that supports the aperture wheel 47 and the eyepiece 48 on the axis 41B in FIG. 4. A portion of the aperture wheel 47 extends through a slot in wall 60 allowing the examiner to center the various apertures on axis 41B shown in FIG. 4. In addition, the end wall 81 contains two notches 82 and 83 in an exterior portion of the wall. These notches are offset on opposite sides of the eyepiece 48. They allow the patient to position his nose with respect to the housing during examination. For example, the patient would position his nose in the notch 82 during examination of his right eye.

From the foregoing discussion, it will be apparent that the retinal acuity tester disclosed in FIGS. 7A and 7B is compact and easy to construct. All the optical elements, except the grating 45, are conventional elements that are readily available and relatively inexpensive. Such elements are used because the retinal acuity tester is an example of a common path interferometer and because the fringes are not subject to thermal variations, vibrations or other environmental perturbations.

In summary, there has been disclosed a basic inteferometer construction that utilizes a holographically recorded grating for projecting stable, high-contrast fringe patterns with high efficiency for testing retinal acuity.

It will be apparent from the foregoing discussion, however, that the specific embodiments of this invention that have been disclosed are merely representative. The basic principles can be employed in a wide variety of applications with the attainment of some or all of the advantages of this invention. Therefore, it is an object of the appended claims to cover all such variations and modifications as come within the true spirit and scope of this invention.

What I claim as new and desire to secure by Letters Patent of the United States is:

1. Opthalmic apparatus for producing an interference pattern on the retina of an eye, said apparatus comprising;
    A. interference pattern generating means for generating a first diffraction and a second diffraction that are of different order, that have equal strength and that overlap thereby to produce a high-contrast, low-noise interference pattern in the area of overlap, and
    B. focusing means positioned to receive the interference pattern from said interference pattern generating means for projecting the interference pattern onto the retina from only two point sources of light in the eye pupil.

2. An apparatus as recited in claim 1 wherein said interference pattern generating means includes:
    i. quasi monochromatic, spatially coherent light source means, and
    ii. holographically recorded, single frequency phase grating means responsive to the energy from said light source means for producing the diffractions.

3. Apparatus as recited in claim 2 additionally comprising:
    C. second focusing means between said light source means and said grating means for focusing the light at a focal point that is displaced toward said light source means from said grating means, and
    D. positioning means connected to said second focusing means and said grating means for moving the focal point with respect to the grating means thereby to vary the interference pattern.

4. Apparatus as recited in claim 3 wherein said second focusing means includes:
    i. negative lens means for receiving light from said light source means,
    ii. objective lens means for focusing light from said negative lens means at the focal point, and
    iii. filter means connected between said light source means and said negative lens means for varying the intensity of the light from said light source means.

5. Apparatus as recited in claim 1 wherein said focusing means comprises:
    i. eye piece means, and
    ii. aperture means positioned between said grating means and said eye piece means.

6. Apparatus as recited in claim 5 additionally comprising optical viewing means interposed between said eye piece means and said grating means for enabling the viewing of the eye through said eye piece means.

7. Apparatus as recited in claim 6 wherein the interference pattern from said grating means is projected along an axis, said optical viewing means comprising:
    i. beamsplitting means disposed on the axis between said grating means and said eye piece means,
    ii. second light source means for projecting light orthogonally to the axis to said beamsplitting means, said beamsplitting means thereby directing the light through said eye piece means to the eye, and
    iii. viewing means for receiving reflected light from said eye piece means through said beamsplitting means for viewing the eye.

8. Apparatus as recited in claim 7 wherein said viewing means comprises cross polarizing means on said axis.

9. Apparatus as recited in claim 7 wherein said optical viewing means includes:
    i. second beamsplitting means disposed on said axis between said first beamsplitting means and said grating means,
    ii. eye piece means aligned on a viewing axis intercepting said second beamsplitting means and said first axis, iii. first and second cross polarizing means disposed on the viewing axis between said eyepiece and said second beamsplitting means and on said first axis between said grating means and said second beamsplitting means, iv. lens means disposed between said first cross polarizing means and said second beamsplitting means for producing a viewable image, and v. mirror means disposed on an extension of the viewing axis on a side of said second beamsplitting means opposite to said lens means.

10. Apparatus as recited in claim 5 wherein said focusing means additionally comprises:

i. dove prism means disposed on the axis between said grating means and said eye piece means, and ii. means for rotating said dove prism thereby to rotate the interference pattern produced on the retina.

* * * * *